United States Patent [19]

Lodge

[11] 4,063,792

[45] Dec. 20, 1977

[54] SLIP-RING CONNECTION

[75] Inventor: James Alec Lodge, Maidenhead, England

[73] Assignee: EMI Limited, Hayes, England

[21] Appl. No.: 757,506

[22] Filed: Jan. 7, 1977

[30] Foreign Application Priority Data

Jan. 29, 1976 United Kingdom ............... 3615/76

[51] Int. Cl.² ........................................... H01R 39/00
[52] U.S. Cl. ................................. 339/5 L; 250/363 R
[58] Field of Search .............. 339/5 L, 5 R, 5 M, 5 S; 250/360, 362, 363, 510

[56] References Cited

U.S. PATENT DOCUMENTS

| 1,669,653 | 5/1928 | Campbell ............................ 339/5 L |
| 2,537,714 | 1/1951 | Spielman ............................ 339/5 R |
| 3,778,614 | 12/1973 | Hounsfield ..................... 250/363 X |
| 3,881,110 | 4/1975 | Hounsfield et al. ............. 250/510 X |

FOREIGN PATENT DOCUMENTS 1,130,490  5/1962  Germany ............................ 339/5 L Primary Examiner—Roy Lake
Assistant Examiner—DeWalden W. Jones
Attorney, Agent, or Firm—Cooper, Dunham, Clark, Griffin & Moran

[57] ABSTRACT

For transfer of electrical energy at high voltage between relatively moving parts it is known to use slip rings and cooperating brushes immersed in insulating liquid. A liquid insulated slip ring connection is described, in which one part is caused to pass through a reservoir of insulating liquid to maintain the insulation without complete immersion and consequent rotating liquid seals. In one example the reservoir itself is formed on the moving part and the liquid is distributed by the forces of rotation.

10 Claims, 1 Drawing Figure

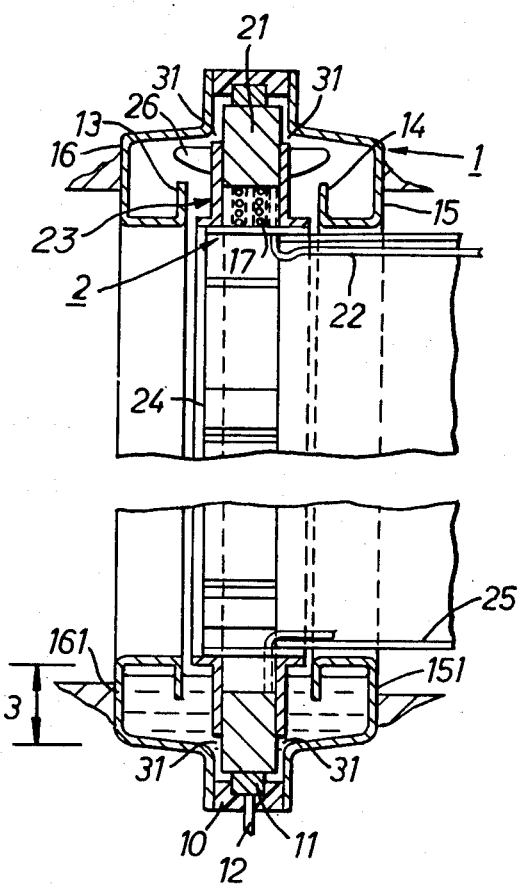

SLIP-RING CONNECTION

This invention relates to a slip-ring electrical connection between relatively movable objects.

Electrical slip-ring connections are used to conduct electricity between one part of an electrical apparatus and a relatively movable part, which may a rotatable or reciprocatable object. The use of unsatisfactory flexible connections can thus be avoided. The apparatus may be an X-ray generating apparatus for examination of a patient or article. For a high voltage, for exampel tens or hundreds of kilo volts, it is known to immerse the brush and ring contact area in an insulating liquid such as oil. When the movement is rapid, e.g. some 3 meters persecond, problems can arise in containing the liquid. It is an object of the invention to provide an improved liquid-immersed electrical slip-ring connection.

According to the invention there is porvided a slip-ring connection which is effectively immersed in an insulating liquid when in motion, to provide an electrical connection between relatively movable parts of an apparatus, the slip-ring connection including first and second relatively movable co-axial annular parts, a slip-ring mounted on one of the annular parts and one or more electrically conducting brushes mounted on the other, wherein the first part is shaped to form a reservoir, open on one side, to retain insulating liquid and the second part is shaped and mounted to project at least in part into the opening in the first part to bring the slip-ring and the one or more brushes into contact within the reservoir, the arrangement being such that the contact surface between the slip-ring and brushes is immersed in the liquid at the lowest point of the reservoir when the relatively movable parts are at rest and such that the insulating liquid is carried to substantially all parts of the contact surface as a result of the relative motion.

The apparatus may be an X-ray apparatus in which the X-rays are generated by a source mounted on a movable part of the apparatus to permit an X-ray beam to be scanned in relation to a patient or article to be examined.

Embodiments of the invention will now be described with reference to the accompanying drawing which shows in cross-section an electrical slip-ring connection including an oil-bath, part of the ring being omitted so that the relatively small cross-section can be shown in more detail.

In electrical apparatus having relatively movable parts it is sometimes necessary to transfer a high voltage, for example some tens or hundreds of kilo volts, between the parts. A slip-ring connection, comprising a conductive track and a localised brush contact to give an electrical connection, are well known for such transfer at lower voltages but as the voltage increases insulation problems increase. To reduce such problems oil immersion has been proposed. However, oil seals are costly and absorb excessive power especially at high speeds.

It is now proposed that the contact area of the brush and ring be extended around the surface of the ring and be immersed in oil or a similar material which will insulate the contact area, when the brush and ring are moving at high relative speed. Typical relative speeds are of the order of 3 meters/second, for a slip-ring connection of a meter or more in diameter. Suitable oil is well known for insulating and cooling electrical transformers. An arrangement will now be described in which oil or similar material, suitably contained when the slip-ring connection is both moving and at rest, is extended around the surface and retained by the forces of rotation when the system is in motion.

Referring now to the drawing there is shown in side elevation and cross-section the construction of one example of a slip-ring connection.

The example shown is for transfer of electrical energy at high voltage between the two relatively moving parts of a computerised axial tomographic X-ray apparatus. Examples of such apparatus are described in U.S. Pat. Nos. 3778614 and 3881110. Both of these specifications show apparatus having a part, rotating relative to other parts about an axis, and carrying an X-ray source to which electrical connections should be made. In this example it will be assumed initially that part 1 is a generally ring-like member rotatable about part 2 which is a fixed ring-like member on the same axis. Part 2 includes a support tube 25 extending whihin the part 1. Tube 25 connects the part 2 with the stationary parts of the X-ray apparatus and is large enough to allow a patient to be moved into or through its aperture.

Tube 25 supports a brush carrier 23, in which a plurality of brushes 21 are supported. Brushes 21 are capable of a limited radial movement from the axis of member 2 and are biassed to the outward extreme by appropriate means such as springs 17. Flexible connections 22 extend back from the brushes 21 to a suitable common terminal, not shown. The brush carrier 23 can be in flanged sections held together by means such as straps 24 and may be of insulating material if that is either desired or necessary. The brushes 21 may be of carbon or carbon fibre.

Part 1 comprises two ring-shaped members 15 and 16 separated by an insulating ring 10. Ring 10 has inset therein a slip ring track 11, formed of metal such as brass plated with rhodium or gold. Electrical connections 12 extend through ring 10 from track 11 to provide the required connection to equipment, such as the X-ray tube (not shown), mounted on the moving parts of the X-ray apparatus. The brushes 21 are urged against the slip-ring track 11 by the action of springs 17.

Members 15 and 16 have flanges 151 and 161 which are joined to the moving parts of the X-ray apparatus as indicated. They are shaped to form a trough of depth shown by the arrow 3 with a deeper section over the insulating ring 10. At the lower part of the assembly the trough thus formed is filled with an electrically insulating fluid, such as transformer oil, to such a depth that it does not overflow when the brushes and brush holder ring are in place. Another suitable fluid for this use is silicone fluid, or similar, which can be described as an insulating oil.

In operation the rotating parts of the X-ray apparatus are rotated by their associated driving means, as indicated in the said patents. Part 1, which is joined to those rotating parts, consequently rotates about part 2 providing a rotating electrical contact through brushes 21. The brushes are kept in contact with the track by virtue of their spring loading.

The oil in the trough tends to remain at the lowest point of the ring but, as a result of the rapid motion of part 1 is in fact dragged around throughout the motion. The forces of rotation cause the oil to collect at the lowest points 31 of the trough, above insulating ring 10, all around that ring and thus the brushes 21 and slip-ring 11 are coated with oil for all contact points around the total 360°. Flanges such as 13 and 14 act as oil catchers or flingers in known manner to prevent the discharge of stray oil in splashes from the arrangement. It can be seen therefore that the arrangement provides a substantially continuous oil bath for the brush/slip-ring contacts, provided the angular velocity of part 1 is sufficiently high.

In an alternative arrangement slip-ring part 1 may be kept fixed and brush part 2 rotated, being appropriately fixed to the rotating parts of the X-ray apparatus. For that arrangement paddles such as 26 may be provided to pick up and distribute the oil all around the contact area, inside the slip-ring at regions 31, in the absence of the rotational forces on the oil.

Preferably the brushes 21 should extend all around the periphery of part 2, as a single brush or a plurality in substantial abutment, to reduce splashing of the oil. It will be appreciated that the positions of the brushes and the slip-ring track can be reversed if desired.

The slip-ring connection need not be provided on the periphery of the inner ring part but could be on one side of that part, towards the periphery, with the fixed contact adjacent at the same radious from the axis.

What I calim is:

1. A slip-ring connection which is effectively immersed in an insulating liquid when in motion, to provide an electrical connection between relatively movable parts of an apparatus, the slip-ring connection including first and second relatively movable co-axial annular parts, a slip-ring mounted on one of the annular parts and one or more electrically conducting brushes mounted on the other, wherein the first part is shaped to form a reservoir, open on one side, to retain insulating liquid and the second part is shaped and mounted to project at least in part into the opening in the first part to bring the slip-ring and the one or more brushes into contact with the reservoir, the arrangement being such that the contact surface between the slip-ring and brushes is immersed in the liquid at the lowest point of the reservoir when the relatively movable parts are at rest and such that the insulating liquid is carried to substantially all parts of the contact surface as a result of the relative motion.

2. A slip-ring connection according to claim 1 including means for preventing excessive discharge of liquid from the arrangement as a result of said relative motion.

3. A slip-ring connection according to claim 1 in which the said second part is maintained stationary and the first part is rotatable about the common axis and in which the liquid can be distributed over the connection between brush and slip-ring by rotational forces.

4. A slip-ring connection according to claim 1 in which the said first part is maintained stationary and the said second part is rotatable about the common axis and including means for distributing the liquid about the inside surface of the first part with rotation of the second part.

5. A slip-ring connection according to claim 4 wherein the means for distributing comprises at least one paddle member fixed to the second part such as to pass through the liquid reservoir in the course of the rotation.

6. A slip-ring connection according to claim 1 wherein the insulating liquid comprises an insulating oil.

7. A slip-ring connection according to claim 1 wherein the slip-ring is mounted on the first part and the one or more conducting brushes are mounted on the second part.

8. In a diagnostic X-ray system having a stationary subsystem and a rotating subsystem, a slip-ring device for providing an electrical connection between the two subsystems, said device comprising: first and second annular parts which move relative to each other about a common axis which is transverse to the vertical direction, one of said parts being supported by the stationary subsystem and the other by the roatating subsystem; an electrically conductive slip-ring mounted on one of the annular parts and one or more electrically conductive brushes mounted on the other; the first part being shaped to form a reservoir open on one side, and insulating liquid contained in said reservoir; the two parts being disposed relative to each other to bring the slip-ring and the one or more brushes in physical and electrical contact with each other within at least a portion of said reservoir, at least a part of the portions of the slip-ring and one or more brushes which are in said contact with each other being immersed in said liquid when the two relatively movable annular parts are at rest with respect to each other, and the two annular parts when moving relative to each other carrying the liquid to all of the contact area of the slip-ring and one or more brushes; and electrical connections between the slip-ring and one of the subsystems and the one or more brushes and the other subsystem.

9. A device as in claim 8 including means for affixing the slip-ring to the first annular part and for affixing the first annular part to the stationary subsystem.

10. A device as in claim 8 wherein the first and second annular parts are out of physical contact with each other except for the contact between the slip-ring and the one or more brushes and including means for directing liquid which has been carried upwardly by the relative movement of the two annular parts to flow downwardly within the reservoir, said directing means including flanges disposed at the open side of the reservoir and extending into the reservoir.

* * * * *